US008568447B2

(12) United States Patent
Chanduszko

(10) Patent No.: US 8,568,447 B2
(45) Date of Patent: Oct. 29, 2013

(54) DELIVERY SYSTEMS AND METHODS FOR PFO CLOSURE DEVICE WITH TWO ANCHORS

(71) Applicant: W.L. Gore & Associates, Inc., Flagstaff, AZ (US)

(72) Inventor: Andrzej J. Chanduszko, Chandler, AZ (US)

(73) Assignee: W.L. Gore & Associates, Inc., Flagstaff, AZ (US)

( * ) Notice: Subject to any disclaimer, the term of this patent is extended or adjusted under 35 U.S.C. 154(b) by 0 days.

(21) Appl. No.: 13/651,643

(22) Filed: Oct. 15, 2012

(65) Prior Publication Data

US 2013/0072965 A1    Mar. 21, 2013

Related U.S. Application Data

(63) Continuation of application No. 11/110,975, filed on Apr. 20, 2005, now Pat. No. 8,308,760.

(60) Provisional application No. 60/568,527, filed on May 6, 2004.

(51) Int. Cl.
 *A61B 17/08* (2006.01)
(52) U.S. Cl.
 USPC .......................................... 606/213; 606/215
(58) Field of Classification Search
 USPC .............. 606/108, 139, 151, 213, 215, 216; 623/1.36, 23.72, 23.76
 See application file for complete search history.

(56) References Cited

U.S. PATENT DOCUMENTS

| | | |
|---|---|---|
| 3,294,631 A | 12/1966 | Mancusi |
| 3,824,631 A | 7/1974 | Burstein et al. |
| 3,874,238 A | 4/1975 | King et al. |
| 3,875,648 A | 4/1975 | Bone |
| 3,924,631 A | 12/1975 | Mancusi, Jr. |
| 4,006,747 A | 2/1977 | Kronenthal et al. |
| 4,007,743 A | 2/1977 | Blake |
| 4,149,327 A | 4/1979 | Hammer et al. |
| 4,425,908 A | 1/1984 | Simon |
| 4,610,674 A | 9/1986 | Suzuki et al. |
| 4,626,245 A | 12/1986 | Weinstein |

(Continued)

FOREIGN PATENT DOCUMENTS

| | | |
|---|---|---|
| DE | 9413645 U1 | 10/1994 |
| EP | 0362113 A1 | 4/1990 |

(Continued)

OTHER PUBLICATIONS

Anthanasiou, T., "Coronary Artery Bypass with the Use of a Magnetic Distal Anastomotic Device: Surgical Technique and Preliminary Experience", *The Heart Surgery Forum #2004-1024*, 2004, 4 pgs.

(Continued)

*Primary Examiner* — Dianne Dornbusch
(74) *Attorney, Agent, or Firm* — DLA Piper LLP (US)

(57) ABSTRACT

A device closes septal openings, such as a patent foramen ovale (PFO). The device includes two anchors and a flexible connector. Tension applied to one or more strings attached to the device causes the device to collapse into a reduced profile form for withdrawal into a delivery catheter, thereby facilitating retrieval of the device after insertion into a septal opening.

7 Claims, 13 Drawing Sheets

(56) References Cited

U.S. PATENT DOCUMENTS

| | | |
|---|---|---|
| 4,693,249 A | 9/1987 | Schenck et al. |
| 4,696,300 A | 9/1987 | Anderson |
| 4,710,181 A | 12/1987 | Fuqua |
| 4,710,192 A | 12/1987 | Liotta et al. |
| 4,738,666 A | 4/1988 | Fuqua |
| 4,836,204 A | 6/1989 | Landymore et al. |
| 4,840,623 A | 6/1989 | Quackenbush |
| 4,902,508 A | 2/1990 | Badylak et al. |
| 4,915,107 A | 4/1990 | Rebuffat et al. |
| 4,917,089 A | 4/1990 | Sideris |
| 4,921,479 A | 5/1990 | Grayzel |
| 4,956,178 A | 9/1990 | Badylak et al. |
| 5,021,059 A * | 6/1991 | Kensey et al. ............ 606/213 |
| 5,037,433 A | 8/1991 | Wilk et al. |
| 5,041,129 A | 8/1991 | Hayhurst et al. |
| 5,049,131 A | 9/1991 | Deuss |
| 5,078,736 A | 1/1992 | Behl |
| 5,106,913 A | 4/1992 | Yamaguchi et al. |
| 5,108,420 A | 4/1992 | Marks |
| 5,149,327 A | 9/1992 | Oshiyama et al. |
| 5,163,131 A | 11/1992 | Row et al. |
| 5,167,363 A | 12/1992 | Adkinson et al. |
| 5,167,637 A | 12/1992 | Okada et al. |
| 5,171,259 A * | 12/1992 | Inoue ............ 606/213 |
| 5,176,659 A | 1/1993 | Mancini |
| 5,192,301 A | 3/1993 | Kamiya et al. |
| 5,222,974 A | 6/1993 | Kensey et al. |
| 5,226,879 A | 7/1993 | Ensminger et al. |
| 5,236,440 A | 8/1993 | Hlavacek |
| 5,245,023 A | 9/1993 | Peoples et al. |
| 5,245,080 A | 9/1993 | Aubard et al. |
| 5,250,430 A | 10/1993 | Peoples et al. |
| 5,257,637 A | 11/1993 | El Gazayerli |
| 5,275,826 A | 1/1994 | Badylak et al. |
| 5,282,827 A | 2/1994 | Kensey et al. |
| 5,284,488 A | 2/1994 | Sideris |
| 5,304,184 A | 4/1994 | Hathaway et al. |
| 5,312,341 A | 5/1994 | Turi |
| 5,312,435 A | 5/1994 | Nash et al. |
| 5,316,262 A | 5/1994 | Koebler |
| 5,320,611 A | 6/1994 | Bonutti et al. |
| 5,334,217 A | 8/1994 | Das |
| 5,350,363 A | 9/1994 | Goode et al. |
| 5,354,308 A | 10/1994 | Simon et al. |
| 5,364,356 A | 11/1994 | Hofling |
| 5,411,481 A | 5/1995 | Allen et al. |
| 5,411,520 A * | 5/1995 | Nash et al. ............ 606/213 |
| 5,413,584 A | 5/1995 | Schulze et al. |
| 5,417,699 A | 5/1995 | Klein et al. |
| 5,425,744 A | 6/1995 | Fagan et al. |
| 5,433,727 A | 7/1995 | Sideris |
| 5,451,235 A | 9/1995 | Lock et al. |
| 5,453,099 A | 9/1995 | Lee et al. |
| 5,478,353 A | 12/1995 | Yoon |
| 5,480,353 A | 1/1996 | Garza, Jr. |
| 5,480,424 A | 1/1996 | Cox |
| 5,486,193 A | 1/1996 | Bourne et al. |
| 5,507,811 A | 4/1996 | Koike et al. |
| 5,534,432 A | 7/1996 | Peoples et al. |
| 5,540,712 A | 7/1996 | Kleshinski et al. |
| 5,562,632 A | 10/1996 | Davila et al. |
| 5,577,299 A | 11/1996 | Thompson et al. |
| 5,601,571 A | 2/1997 | Moss |
| 5,603,703 A | 2/1997 | Elsberry et al. |
| 5,618,311 A | 4/1997 | Gryskiewicz |
| 5,620,461 A | 4/1997 | Muijs Van De Moer et al. |
| 5,626,599 A | 5/1997 | Bourne et al. |
| 5,634,936 A | 6/1997 | Linden et al. |
| 5,649,950 A | 7/1997 | Bourne et al. |
| 5,649,959 A | 7/1997 | Hannam et al. |
| 5,662,681 A * | 9/1997 | Nash et al. ............ 606/213 |
| 5,663,063 A | 9/1997 | Peoples et al. |
| 5,683,411 A | 11/1997 | Kavteladze et al. |
| 5,690,674 A | 11/1997 | Diaz |
| 5,693,085 A | 12/1997 | Buirge et al. |
| 5,702,421 A | 12/1997 | Schneidt et al. |
| 5,709,707 A | 1/1998 | Lock et al. |
| 5,713,864 A | 2/1998 | Verkaart |
| 5,717,259 A | 2/1998 | Schexnayder |
| 5,720,754 A | 2/1998 | Middleman et al. |
| 5,725,552 A | 3/1998 | Kotula et al. |
| 5,733,294 A | 3/1998 | Forber et al. |
| 5,733,337 A | 3/1998 | Carr, Jr. et al. |
| 5,741,297 A | 4/1998 | Simon |
| 5,772,641 A | 6/1998 | Wilson |
| 5,776,162 A | 7/1998 | Kleshinski |
| 5,776,183 A | 7/1998 | Kanesaka et al. |
| 5,797,960 A | 8/1998 | Stevens et al. |
| 5,800,516 A | 9/1998 | Fine et al. |
| 5,810,884 A | 9/1998 | Kim |
| 5,820,594 A | 10/1998 | Fontirroche et al. |
| 5,823,956 A | 10/1998 | Roth et al. |
| 5,829,447 A | 11/1998 | Stevens et al. |
| 5,853,420 A | 12/1998 | Chevillon et al. |
| 5,853,422 A | 12/1998 | Huebsch et al. |
| 5,855,614 A | 1/1999 | Stevens et al. |
| 5,861,003 A | 1/1999 | Latson et al. |
| 5,865,791 A | 2/1999 | Whayne et al. |
| 5,879,366 A | 3/1999 | Shaw et al. |
| 5,893,856 A | 4/1999 | Jacob et al. |
| 5,902,287 A | 5/1999 | Martin |
| 5,902,319 A | 5/1999 | Daley |
| 5,904,703 A | 5/1999 | Gilson |
| 5,919,200 A | 7/1999 | Stambaugh et al. |
| 5,924,424 A | 7/1999 | Stevens et al. |
| 5,928,250 A | 7/1999 | Koike et al. |
| 5,944,691 A | 8/1999 | Querns et al. |
| 5,944,738 A | 8/1999 | Amplatz et al. |
| 5,955,110 A | 9/1999 | Patel et al. |
| 5,976,174 A | 11/1999 | Ruiz |
| 5,980,505 A | 11/1999 | Wilson |
| 5,989,268 A | 11/1999 | Pugsley, Jr. et al. |
| 5,993,475 A | 11/1999 | Lin et al. |
| 5,993,844 A | 11/1999 | Abraham et al. |
| 5,997,575 A | 12/1999 | Whitson et al. |
| 6,010,447 A | 1/2000 | Kardjian |
| 6,010,517 A | 1/2000 | Baccaro |
| 6,019,753 A | 2/2000 | Pagan |
| 6,024,756 A | 2/2000 | Huebsch et al. |
| 6,027,519 A | 2/2000 | Stanford |
| 6,030,007 A * | 2/2000 | Bassily et al. ............ 289/1.5 |
| 6,056,760 A | 5/2000 | Koike et al. |
| 6,071,998 A | 6/2000 | Muller et al. |
| 6,077,291 A | 6/2000 | Das |
| 6,077,880 A | 6/2000 | Castillo et al. |
| 6,079,414 A | 6/2000 | Roth |
| 6,080,182 A | 6/2000 | Shaw et al. |
| 6,096,347 A | 8/2000 | Geddes et al. |
| 6,106,913 A | 8/2000 | Scardino et al. |
| 6,113,609 A | 9/2000 | Adams |
| 6,117,159 A | 9/2000 | Huebsch et al. |
| 6,126,686 A | 10/2000 | Badylak et al. |
| 6,132,438 A | 10/2000 | Fleischman et al. |
| 6,143,037 A | 11/2000 | Goldstein et al. |
| 6,152,144 A | 11/2000 | Lesh et al. |
| 6,152,935 A | 11/2000 | Kammerer et al. |
| 6,165,183 A | 12/2000 | Kuehn et al. |
| 6,165,204 A | 12/2000 | Levinson et al. |
| 6,168,588 B1 | 1/2001 | Wilson |
| 6,171,329 B1 | 1/2001 | Shaw et al. |
| 6,174,322 B1 * | 1/2001 | Schneidt ............ 606/213 |
| 6,174,330 B1 | 1/2001 | Stinson |
| 6,183,443 B1 | 2/2001 | Kratoska et al. |
| 6,187,039 B1 | 2/2001 | Hiles et al. |
| 6,190,353 B1 | 2/2001 | Makower et al. |
| 6,190,357 B1 | 2/2001 | Ferrari et al. |
| 6,197,016 B1 | 3/2001 | Fourkas et al. |
| 6,199,262 B1 | 3/2001 | Martin |
| 6,206,895 B1 | 3/2001 | Levinson |
| 6,206,907 B1 | 3/2001 | Marino et al. |
| 6,214,029 B1 | 4/2001 | Thill et al. |
| 6,217,590 B1 | 4/2001 | Levinson |
| 6,221,092 B1 | 4/2001 | Koike et al. |
| 6,227,139 B1 | 5/2001 | Nguyen et al. |

(56) References Cited

U.S. PATENT DOCUMENTS

| | | |
|---|---|---|
| 6,228,097 B1 | 5/2001 | Levinson et al. |
| 6,231,561 B1 | 5/2001 | Frazier et al. |
| 6,245,080 B1 | 6/2001 | Levinson |
| 6,245,537 B1 | 6/2001 | Williams et al. |
| 6,261,309 B1 | 7/2001 | Urbanski |
| 6,265,333 B1 | 7/2001 | Dzenis et al. |
| 6,270,515 B1 | 8/2001 | Linden et al. |
| 6,277,138 B1 | 8/2001 | Levinson et al. |
| 6,277,139 B1 | 8/2001 | Levinson et al. |
| 6,287,317 B1 | 9/2001 | Makower et al. |
| 6,290,674 B1 | 9/2001 | Roue et al. |
| 6,299,635 B1 | 10/2001 | Frantzen |
| 6,306,150 B1 | 10/2001 | Levinson |
| 6,306,424 B1 | 10/2001 | Vyakarnam et al. |
| 6,312,443 B1 | 11/2001 | Stone |
| 6,312,446 B1 | 11/2001 | Huebsch et al. |
| 6,315,791 B1 | 11/2001 | Gingras et al. |
| 6,316,262 B1 | 11/2001 | Huisman et al. |
| 6,319,263 B1 | 11/2001 | Levinson |
| 6,322,548 B1 | 11/2001 | Payne et al. |
| 6,328,727 B1 | 12/2001 | Frazier et al. |
| 6,334,872 B1 | 1/2002 | Termin et al. |
| 6,342,064 B1 | 1/2002 | Koike et al. |
| 6,344,048 B1 | 2/2002 | Chin et al. |
| 6,344,049 B1 | 2/2002 | Levinson et al. |
| 6,346,074 B1 | 2/2002 | Roth |
| 6,348,041 B1 | 2/2002 | Klint et al. |
| 6,352,552 B1 | 3/2002 | Levinson et al. |
| 6,355,052 B1 | 3/2002 | Neuss et al. |
| 6,356,782 B1 | 3/2002 | Sirimanne et al. |
| 6,358,238 B1 | 3/2002 | Sherry |
| 6,364,853 B1 | 4/2002 | French et al. |
| 6,371,904 B1 | 4/2002 | Sirimanne et al. |
| 6,375,625 B1 | 4/2002 | French et al. |
| 6,375,671 B1 | 4/2002 | Kobayashi et al. |
| 6,379,342 B1 | 4/2002 | Levinson |
| 6,379,368 B1 | 4/2002 | Corcoran et al. |
| 6,387,104 B1 | 5/2002 | Pugsley, Jr. et al. |
| 6,398,796 B2 | 6/2002 | Levinson |
| 6,402,772 B1 | 6/2002 | Amplatz et al. |
| 6,419,669 B1 | 7/2002 | Frazier et al. |
| 6,426,145 B1 | 7/2002 | Moroni |
| 6,436,088 B2 | 8/2002 | Frazier et al. |
| 6,440,152 B1 | 8/2002 | Gainor et al. |
| 6,450,987 B1 | 9/2002 | Kramer |
| 6,460,749 B1 | 10/2002 | Levinson et al. |
| 6,482,224 B1 | 11/2002 | Michler et al. |
| 6,488,706 B1 | 12/2002 | Solymar |
| 6,494,846 B1 | 12/2002 | Margolis |
| 6,494,888 B1 | 12/2002 | Laufer et al. |
| 6,508,828 B1 | 1/2003 | Akerfeldt et al. |
| 6,514,515 B1 | 2/2003 | Williams |
| 6,548,569 B1 | 4/2003 | Williams et al. |
| 6,551,303 B1 | 4/2003 | Van Tassel et al. |
| 6,551,344 B2 | 4/2003 | Thill |
| 6,585,719 B2 | 7/2003 | Wang |
| 6,585,755 B2 | 7/2003 | Jackson et al. |
| 6,596,013 B2 | 7/2003 | Yang et al. |
| 6,599,448 B1 | 7/2003 | Ehrhard, Jr. et al. |
| 6,610,764 B1 | 8/2003 | Martin et al. |
| 6,616,675 B1 | 9/2003 | Evard et al. |
| 6,623,508 B2 | 9/2003 | Shaw et al. |
| 6,623,518 B2 | 9/2003 | Thompson et al. |
| 6,626,936 B2 | 9/2003 | Stinson |
| 6,629,901 B2 | 10/2003 | Huang |
| 6,666,861 B1 | 12/2003 | Grabek |
| 6,669,722 B2 | 12/2003 | Chen et al. |
| 6,689,589 B2 | 2/2004 | Huisman et al. |
| 6,712,804 B2 | 3/2004 | Roue et al. |
| 6,712,836 B1 | 3/2004 | Berg et al. |
| 6,726,696 B1 | 4/2004 | Houser et al. |
| 6,828,357 B1 | 12/2004 | Martin et al. |
| 6,838,493 B2 | 1/2005 | Williams et al. |
| 6,867,247 B2 | 3/2005 | Williams et al. |
| 6,867,248 B1 | 3/2005 | Martin et al. |
| 6,867,249 B2 | 3/2005 | Lee et al. |
| 6,921,410 B2 | 7/2005 | Porter |
| 7,494,496 B2 * | 2/2009 | Swain et al. ............... 606/151 |
| 2001/0010481 A1 | 8/2001 | Blanc et al. |
| 2001/0014800 A1 | 8/2001 | Frazier et al. |
| 2001/0025132 A1 | 9/2001 | Alferness et al. |
| 2001/0034537 A1 | 10/2001 | Shaw et al. |
| 2001/0037129 A1 | 11/2001 | Thill |
| 2001/0039435 A1 | 11/2001 | Roue et al. |
| 2001/0039436 A1 | 11/2001 | Frazier et al. |
| 2001/0041914 A1 | 11/2001 | Frazier et al. |
| 2001/0041915 A1 | 11/2001 | Roue et al. |
| 2001/0044639 A1 | 11/2001 | Levinson |
| 2001/0049492 A1 | 12/2001 | Frazier et al. |
| 2002/0010481 A1 | 1/2002 | Jayaraman |
| 2002/0019648 A1 | 2/2002 | Akerfeldt et al. |
| 2002/0022859 A1 | 2/2002 | Hogendijk |
| 2002/0022860 A1 | 2/2002 | Borillo et al. |
| 2002/0026208 A1 | 2/2002 | Roe et al. |
| 2002/0029048 A1 | 3/2002 | Miller |
| 2002/0032459 A1 | 3/2002 | Horzewski et al. |
| 2002/0032462 A1 | 3/2002 | Houser et al. |
| 2002/0034259 A1 | 3/2002 | Tada |
| 2002/0035374 A1 | 3/2002 | Borillo et al. |
| 2002/0043307 A1 | 4/2002 | Ishida et al. |
| 2002/0049457 A1 | 4/2002 | Kaplan et al. |
| 2002/0052572 A1 | 5/2002 | Franco et al. |
| 2002/0058989 A1 | 5/2002 | Chen et al. |
| 2002/0077555 A1 | 6/2002 | Schwartz |
| 2002/0095174 A1 | 7/2002 | Tsugita et al. |
| 2002/0096183 A1 | 7/2002 | Stevens et al. |
| 2002/0099389 A1 | 7/2002 | Michler et al. |
| 2002/0099390 A1 | 7/2002 | Kaplan et al. |
| 2002/0103492 A1 | 8/2002 | Kaplan et al. |
| 2002/0107531 A1 | 8/2002 | Schreck et al. |
| 2002/0111537 A1 | 8/2002 | Taylor et al. |
| 2002/0111637 A1 | 8/2002 | Kaplan et al. |
| 2002/0111647 A1 | 8/2002 | Khairkhahan et al. |
| 2002/0120323 A1 | 8/2002 | Thompson et al. |
| 2002/0128680 A1 | 9/2002 | Pavlovic |
| 2002/0129819 A1 | 9/2002 | Feldman et al. |
| 2002/0164729 A1 | 11/2002 | Skraly et al. |
| 2002/0169377 A1 | 11/2002 | Khairkhahan et al. |
| 2002/0169478 A1 * | 11/2002 | Schwartz et al. ............. 606/232 |
| 2002/0183786 A1 | 12/2002 | Girton |
| 2002/0183787 A1 | 12/2002 | Wahr et al. |
| 2002/0183823 A1 | 12/2002 | Pappu |
| 2002/0198563 A1 | 12/2002 | Gainor et al. |
| 2003/0004533 A1 | 1/2003 | Dieck et al. |
| 2003/0023266 A1 | 1/2003 | Borillo et al. |
| 2003/0028213 A1 | 2/2003 | Thill et al. |
| 2003/0032979 A1 | 2/2003 | Mortier et al. |
| 2003/0045893 A1 | 3/2003 | Ginn |
| 2003/0050665 A1 | 3/2003 | Ginn |
| 2003/0055455 A1 | 3/2003 | Yang et al. |
| 2003/0057156 A1 | 3/2003 | Peterson et al. |
| 2003/0059640 A1 | 3/2003 | Marton et al. |
| 2003/0065379 A1 | 4/2003 | Babbs et al. |
| 2003/0100920 A1 | 5/2003 | Akin et al. |
| 2003/0120337 A1 | 6/2003 | Van Tassel et al. |
| 2003/0139819 A1 | 7/2003 | Beer et al. |
| 2003/0171774 A1 | 9/2003 | Freudenthal et al. |
| 2003/0191495 A1 * | 10/2003 | Ryan et al. ................. 606/213 |
| 2003/0195530 A1 | 10/2003 | Thill |
| 2003/0204203 A1 | 10/2003 | Khairkhahan et al. |
| 2004/0044361 A1 | 3/2004 | Frazier et al. |
| 2004/0073242 A1 | 4/2004 | Chanduszko |
| 2004/0098121 A1 | 5/2004 | Opolski |
| 2004/0116949 A1 * | 6/2004 | Ewers et al. ................. 606/167 |
| 2004/0133236 A1 * | 7/2004 | Chanduszko ................ 606/213 |
| 2004/0176799 A1 | 9/2004 | Chanduszko et al. |
| 2004/0210301 A1 | 10/2004 | Obermiller |
| 2004/0234567 A1 | 11/2004 | Dawson |
| 2005/0025809 A1 | 2/2005 | Hasirci et al. |
| 2005/0043759 A1 | 2/2005 | Chanduszko |
| 2005/0113868 A1 | 5/2005 | Devellian |
| 2005/0267523 A1 | 12/2005 | Devellian et al. |
| 2005/0273135 A1 | 12/2005 | Chanduszko et al. |
| 2005/0288786 A1 | 12/2005 | Chanduszko |

(56) References Cited

U.S. PATENT DOCUMENTS

| | | |
|---|---|---|
| 2006/0122647 A1 | 6/2006 | Callaghan et al. |
| 2006/0265004 A1 | 11/2006 | Callaghan et al. |
| 2006/0271089 A1 | 11/2006 | Alejandro et al. |
| 2007/0010851 A1 | 1/2007 | Chanduszko et al. |
| 2007/0167981 A1 | 7/2007 | Opolski |

FOREIGN PATENT DOCUMENTS

| | | |
|---|---|---|
| EP | 0474887 A1 | 3/1992 |
| EP | 0839549 A1 | 5/1998 |
| EP | 0861632 | 9/1998 |
| EP | 1013227 A2 | 6/2000 |
| EP | 1046375 A1 | 10/2000 |
| EP | 1222897 A2 | 7/2002 |
| WO | WO 96/25179 A1 | 8/1996 |
| WO | WO 96/31157 A1 | 10/1996 |
| WO | WO 98/07375 A1 | 2/1998 |
| WO | WO 98/08462 | 3/1998 |
| WO | WO 98/16174 | 4/1998 |
| WO | WO 98/29026 A2 | 7/1998 |
| WO | WO 98/51812 | 11/1998 |
| WO | WO 99/05977 A1 | 2/1999 |
| WO | WO 99/18861 | 4/1999 |
| WO | WO 99/18862 A1 | 4/1999 |
| WO | WO 99/18864 A1 | 4/1999 |
| WO | WO 99/18870 A1 | 4/1999 |
| WO | WO 99/18871 A1 | 4/1999 |
| WO | WO 99/30640 A1 | 6/1999 |
| WO | WO 99/66846 | 12/1999 |
| WO | WO 00/27292 A1 | 5/2000 |
| WO | WO 00/44428 A2 | 8/2000 |
| WO | WO 01/008600 | 2/2001 |
| WO | WO 01/19256 | 3/2001 |
| WO | WO 01/21247 A1 | 3/2001 |
| WO | WO 01/28432 | 4/2001 |
| WO | WO 01/30268 A1 | 5/2001 |
| WO | WO 01/49185 A1 | 7/2001 |
| WO | WO 01/78596 A1 | 10/2001 |
| WO | WO 01/93783 | 12/2001 |
| WO | WO 02/17809 A1 | 3/2002 |
| WO | WO 02/24106 A3 | 3/2002 |
| WO | WO 03/024337 A1 | 3/2003 |
| WO | WO 03/053493 A2 | 7/2003 |
| WO | WO 03/059152 | 7/2003 |
| WO | WO 03/063732 | 8/2003 |
| WO | WO 03/077733 A2 | 9/2003 |
| WO | WO 03/082076 | 10/2003 |
| WO | WO 03/103476 A2 | 12/2003 |
| WO | WO 2004/032993 | 4/2004 |
| WO | WO 2004/037333 | 5/2004 |
| WO | WO 2004/043266 | 5/2004 |
| WO | WO 2004/043508 | 5/2004 |
| WO | WO 2004/052213 | 6/2004 |
| WO | WO 2005/006990 | 1/2005 |
| WO | WO 2005/018728 | 3/2005 |
| WO | WO 2005/027752 | 3/2005 |
| WO | WO 2005/074813 | 8/2005 |
| WO | WO 2005/092203 | 10/2005 |
| WO | WO 2005/110240 | 11/2005 |
| WO | WO 2005/112779 | 12/2005 |
| WO | WO 2006/036837 | 4/2006 |
| WO | WO 2006/102213 | 9/2006 |

OTHER PUBLICATIONS

Bachthaler et al., "Corrosion of Tungsten Coils After Peripheral Vascular Embolization Theraphy: Influence on Outcome and Tungsten Load", *Catherization and Cardiovascular Interventions*, vol. 62, pp. 380-384, 2004.
European Examination Report, European Application No. 03729663.9, mailed Jul. 16, 2008 (5 pages).
European Examination Report, European Application No. 03731562.9, mailed Jul. 18, 2008 (3 pages).
European Examination Report, European Application No. 03779297.5, mailed Mar. 15, 2007 (6 pages).
European Examination Report, European Application No. 04781644.2, mailed Aug. 23, 2007 (3 pages).
European Search Report, European Application No. 03729663.9, mailed Feb 20, 2008 (3 pages).
Falk, V., "Facilitated Endoscopic Beating Heart Coronary Artery Bypass Grafting Using a Magentic Coupling Device", *Journal of Thoracic and Cardiovascular Surgery*, 126(5):1575-1579.
Filsoufi et al., "Automated Distal Coronary Bypass with a Novel Magnetic Coupler (MVP system)", J. Thoracic and Cardiovascular Surgery, 127(1):185-192.
International Search Report and Written Opinion, International Patent Application No. PCT/US06/41255, mailed Jun. 13, 2008 (6 pgs.).
International Search Report and Written Opinion, International Patent Application No. PCT/US08/59429, mailed Sep. 5, 2008 (9 pgs.).
International Search Report for International Patent Application No. PCT/AU03/00759, filed Jun. 19, 2003.
International Search Report, International Application No. PCT/US02/40850 mailed Jun. 19, 2003 (4 pgs.).
International Search Report, International Application No. PCT/US03/01050, mailed Jul. 8, 2003 (1 pg.).
International Search Report, International Application No. PCT/US03/09051, mailed Sep. 29, 2003 (2 pgs.).
International Search Report, International Application No. PCT/US03/17390, mailed Oct. 6, 2003 (4 pgs.).
International Search Report, International Application No. PCT/US03/17715, mailed Mar. 24, 2004 (2 pgs.).
International Search Report, International Application No. PCT/US03/32133, mailed Apr. 22, 2004 (1 pg.).
International Search Report, International Application No. PCT/US03/34003 mailed Oct. 3, 2004 (4 pgs.).
International Search Report, International Application No. PCT/US03/35479, mailed Apr. 14, 2004 (2 pgs.).
International Search Report, International Application No. PCT/US03/35998 mailed Jun. 16, 2004 (5 pgs.).
International Search Report, International Application No. PCT/US03/39253, mailed Apr. 19, 2004 (4 pgs.).
International Search Report, International Application No. PCT/US04/022643, mailed Mar. 31, 2005 (2 pgs.).
International Search Report, International Application No. PCT/US04/026998, mailed Apr. 22, 2005 (5 pgs.).
International Search Report, International Application No. PCT/US04/029978, mailed Jan. 26, 2005 (3 pgs.).
International Search Report, International Application No. PCT/US05/006703, mailed Jul. 25, 2005 (3 pgs.).
International Search Report, International Application No. PCT/US05/013705 mailed Aug. 4, 2005 (4 pgs.).
International Search Report, International Application No. PCT/US05/015382, mailed Oct. 6, 2005 (4 pgs.).
International Search Report, International Application No. PCT/US05/34276, mailed Oct. 9, 2007.
International Search Report, International Application No. PCT/US06/009978, mailed Jul. 13, 2006 (2 pgs.).
International Search Report, International Application No. PCT/US07/065546, mailed Oct. 29, 2007 (4 pages).
International Search Report, International Application No. PCT/US2007/065526, mailed Aug. 8, 2007 (5 pgs.).
International Search Report, International Application No. PCT/US2007/065541, mailed Aug. 7, 2007 (4 pgs.).
International Search Report, International Application No. PCT/US97/14822, mailed Feb. 20, 1998 (2 pgs.).
International Search Report, International Application No. PCT/US97/17927, mailed Feb. 10, 1998 (1 pg.).
Kimura et al., "Effects of Neutron Irradiation on the Transformation Behavior in Ti-Ni Alloys", Abstract, *Proceedings of the Inn Conf. on Martensitic Transformations*, 1992, pp. 935-940.
Klima, U., "Magnetic Vascular Port in Minimally Invasive Direct Coronary Artery Bypass Grafting", Circulation, 2004, II-55-II-60.

(56) References Cited

OTHER PUBLICATIONS

Meier, MD, Bernhard, et al., "Contemporary Management of Patent Foramen Ovale," American Heart Association, Inc., *Circulation*, 107:5-9 (2003).

Nat'l Aeronautics and Space Administration, "55-Nitinol—The Alloy with a Memory: Its Physical Metallurgy, Properties and Applications", *NASA Report*, pp. 24-25.

Parviainen et al., "A New Biodegradable Stent for the Pancreaticojejunal Anastomosis After Pancreaticoduodenal Resection: In Vitro Examination and Pilot Experiences in Humans", *Pancreas*, 21(1):14-21 (2000).

Ramanathan et. al., "Experimental and Computational Methods for Shape Memory Alloys," *15th ASCE Engineering Mechanics Conference*, Jun. 2-5, 2002.

Ruddy et al., "Rheological, Mechanical and Thermal Behaviour of Radipaque Filled Polymers", *Polymer Processing Research Centre, School of Chemical Engineering, Queen's University of Belfast*, 5 pages.

Ruiz, et al., The Puncture Technique: A New Method for Transcatheter Closure of Patent Foramen Ovale, *Catheterization and Cardiovascular Interventions*, 53:369-372 (2001).

Shabalovskaya, S., "Surface, Corrosion amd Biocompatibility Aspects of Nitinol as and Implant Material", *Bio-Medical Materials and Engineering*, 12:69-109 (2002).

SMST-2000, "Proceedings of the International Conference on Shape Memory and Superelastic Technologies", Apr. 30 to May 4, 2000, *Asilomar Conference Center*.

Stockel, "Nitinol Medical Devices and Implants", *SMST-2000 Conference Proceedings*, 2001, pp. 531-541.

Uchil, J., "Shape Memory Alloys—Characterization Techniques", *Pramana—Journal of Physics*, 2002, vol. 58(5)(6), pp. 1131-1139.

Vaajanen et al., "Expansion and Fixation Properties of a New Braided Biodegradable Urethral Stent: An Experimental Study in the Rabbit", *The Journal of Urology*, 169:1771-1174 (2003).

\* cited by examiner

DELIVERY SYSTEMS AND METHODS FOR PFO CLOSURE DEVICE WITH TWO ANCHORS

CROSS-REFERENCE TO RELATED APPLICATIONS

This application is a continuation application of U.S. application Ser. No. 11/110,975 filed Apr. 20, 2005, now U.S. Pat. No. 8,308,760; which claims the benefit under 35 USC §119(e) to U.S. Application Ser. No. 60/568,527 filed May 6, 2004, now expired. The disclosure of each of the prior applications is considered part of and is incorporated by reference in the disclosure of this application.

BACKGROUND OF THE INVENTION

The invention relates to devices and methods that are used to close septal openings, such as a patent foramen ovale (PFO). A PFO is a persistent, one-way, usually flap-like opening in the wall between the right atrium (RA) and left atrium (LA) of the heart. Because left atrial pressure is normally higher than right atrial pressure, the flap usually stays closed. Under certain conditions, however, right atrial pressure can exceed left atrial pressure, which creates the possibility that blood could pass from the right atrium to the left atrium and allow blood clots to enter the systemic circulation. It is desirable to avoid this situation.

SUMMARY OF THE INVENTION

Embodiments of the present invention are directed to devices for closing septal defects such as PFOs, and for delivering and recovering closure devices. The closure devices in these embodiments generally include a proximal anchor, a distal anchor, and a flexible anchor connector for connecting the two anchors. The connector is preferably a flexible elastomeric layer, which can also be used to promote tissue ingrowth or for drug delivery. The flexible material can also be covered with a biocompatible glue to promote adherence to tissue or growth factors to accelerate tissue ingrowth.

In accordance with some embodiments of the invention, options are provided for multiple delivery/recovery of the same device without withdrawing the device from the delivery sheath or otherwise replacing it. Other embodiments include the use of a single use delivery/recovery string that reduces the complexity of the delivery/recovery system and the procedure itself.

These and other features will become apparent from the following detailed description and drawings. The inventions are capable of other and different embodiments and its several details may be capable of modifications in various respects, all without departing from the invention. Accordingly, the drawings and description are to be regarded as illustrative in nature and not in a restrictive or limiting sense.

DETAILED DESCRIPTION OF THE INVENTION

This invention relates to structures of the type shown in application Ser, No. 10/326,535, filed Dec. 19, 2002, published application no. 2003/0191495, which is expressly incorporated herein by reference. This invention includes further embodiments of the device, and methods to allow a physician or other practitioner to deliver and deploy the device in a defect, then recover and remove it if desired from a defect after deployment. Some embodiments allow for multiple deployments and removals of the same occluder. Other embodiments have a single delivery/recovery mechanism requiring a simpler delivery/recovery system. While described for use with a patent foramen ovale (PFO), these systems and methods could be used for occluding or holding together other defects.

Figure 1:
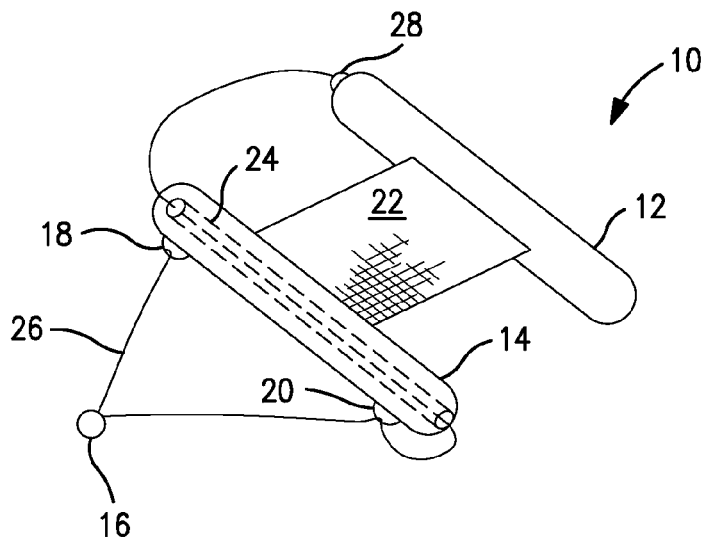
FIG. 1 is a perspective view of a closure device according to a first embodiment.

As shown in FIG. 1, a closure device 10 has a distal anchor 12 for placement on the left atrial side of a PFO, a proximal anchor 14 for placement in the right atrial side of a PFO, a proximal attachment point 16 spaced from anchor 14 for attachment and release from a wire through a catheter on an anchor connector 22 for connecting anchors 12 and 14, and frangible attachment points 18, 20 on anchor 14. A bore 24 is provided along the lengthwise direction in proximal anchor 14. A string 26 extends from attachment point 18 on anchor 14 attachment point 16 to attachment point 20 on anchor 14. The string then runs through bore 24 to the end of anchor 14, and across to a permanent attachment point 28 on anchor 12. Within bore 24, the string can move relative to anchor 14.

In this embodiment and others, the distal anchor, the proximal anchor, and the connectors between the anchor members can each be made of a bioresorbable material.

These components can be fabricated from a single piece of a bioresorbable polymer or by a laminated composite of two or more materials to provide a mix of properties; for example, anchors can have stiff centers and flexible edges, and blood contacting surfaces can have controlled porosity or surface texture to promote fast and thorough endothelialization, while minimizing thrombosis. In addition, the tissue contacting surface of the anchors can be designed to provide added stability, such as being roughened. Other components, such as connection balls and strings, can also be made of bioresorbable materials; e.g., the string can be made of bioresorbable fibers that are braided or otherwise combined for strength.

The anchors are elongated supports, preferably generally cylindrical with rod-like bodies with ends that are atraumatic, and preferably rounded. In size, the distal anchor component could be about 15-30 mm long and 2 mm in diameter with a circular cross-section. The proximal anchor can have similar dimensions and shape, although it can be shorter in overall length. Other distal and proximal anchor structures are also possible. For example, sides of the anchors can be flattened, especially the side which will contact the atrial septum. The generally cylindrical shape for the anchors means that they have at least some portions with generally round cross-sections, but could have one or more flattened sides, cut-outs, or other variations from an "ideal" cylinder.

The anchor connector can be elastomeric and resilient and made from a material, such as polyester, biological tissue, bioresorbable polymer, small diameter springs (e.g., Nitinol), or spongy polymeric material, and can include thrombogenic or inflammatory materials. Alternatively, the anchor connector can be made of multiple strands of material such as polymer fibers. The anchor connector can be textured or porous. These kinds of surfaces can also produce inflammatory responses, and therefore can promote faster tissue ingrowth and faster defect closure.

Figure 2:
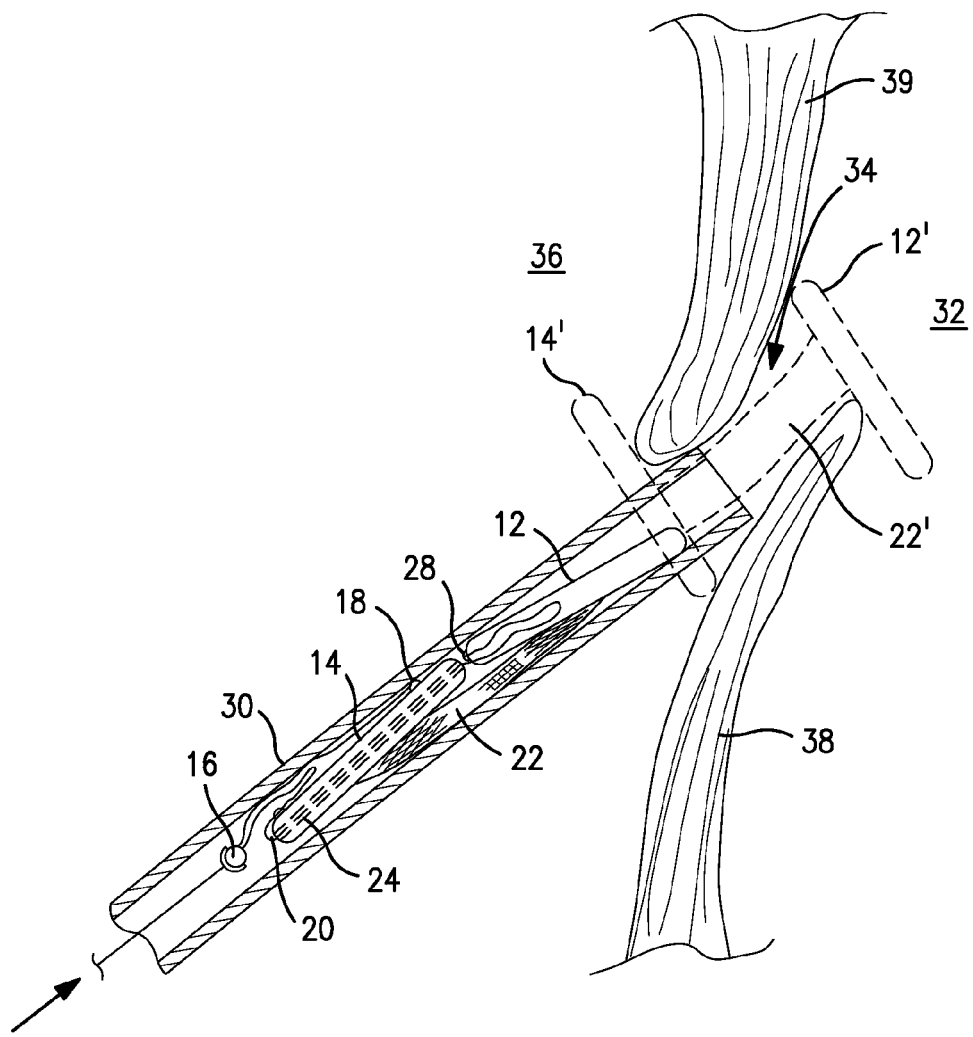
FIGS. 2-7 are partial side and partial cross-sectional views showing the delivery and recovery of a closure device of the type shown in FIG. 1.
Figure 3:
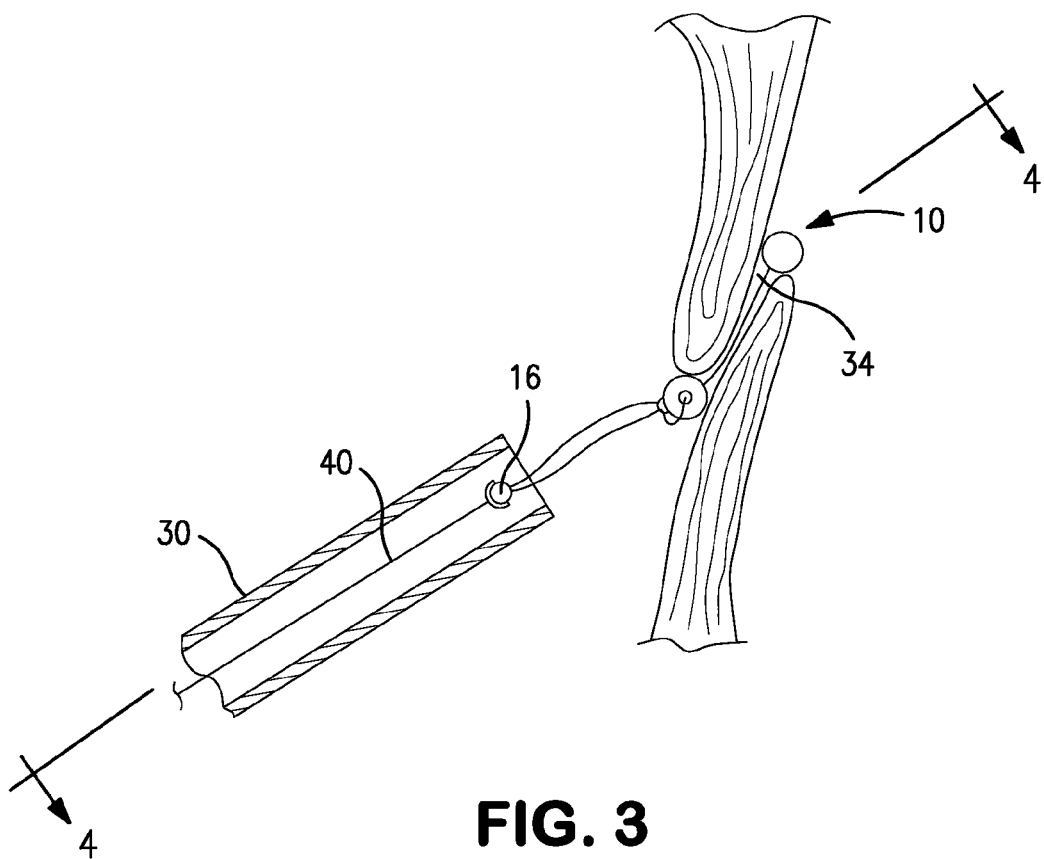
Figure 4:
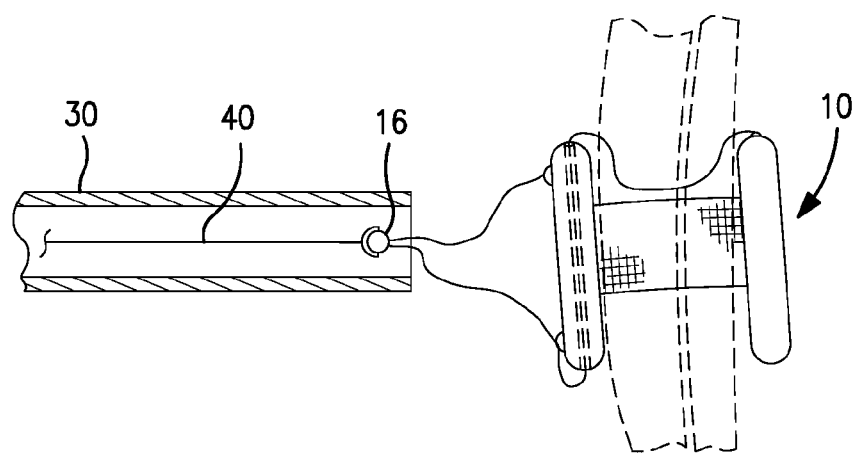

FIGS. 2-4 show the delivery of device 10 to a PFO. Device 10 is shown inside a delivery sheath 30, and represented as delivered in phantom with anchors 12' and 14' and anchor connector 22'. While in the delivery sheath, the string between the anchors has some slack in it. The delivery sheath is introduced so that anchor 12 is positioned in the left atrium 32. This positioning is typically done by providing delivery sheath 30 in or at the edge of left atrium 32 through PFO tunnel 34, and retracting sheath 30 so that anchor 12 is deployed in left atrium 32 against septum primum 38 and septum secundum 39. Sheath 30 is retracted until anchor 14 is deployed in right atrium 36 as indicated in FIG. 2 in phantom. FIGS. 3 and 4 show a side view and a top view of device 10 in PFO tunnel 34. A catheter 40 is maintained in contact with attachment point 16.

Figure 5:
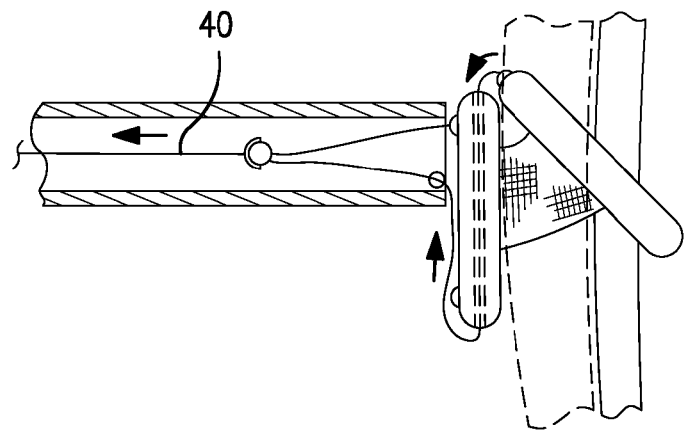
Figure 6:
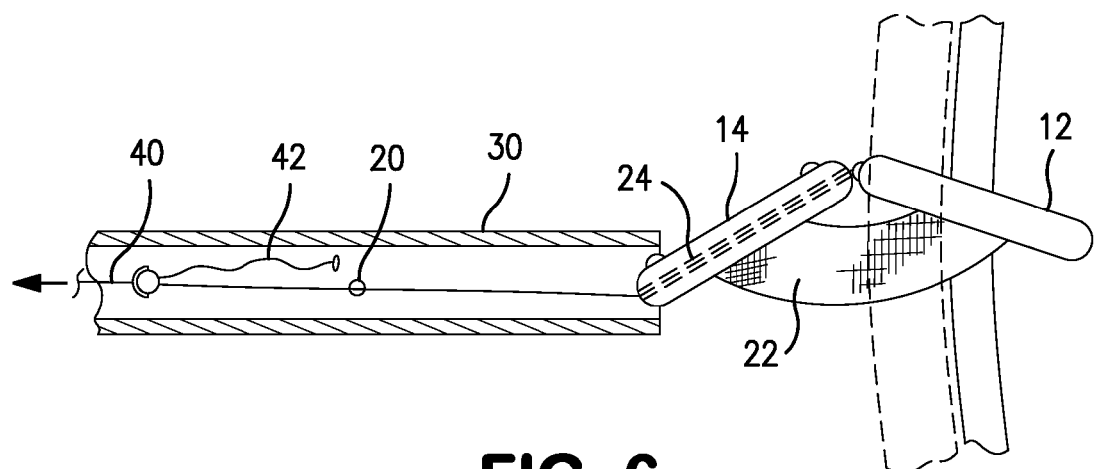
Figure 7:
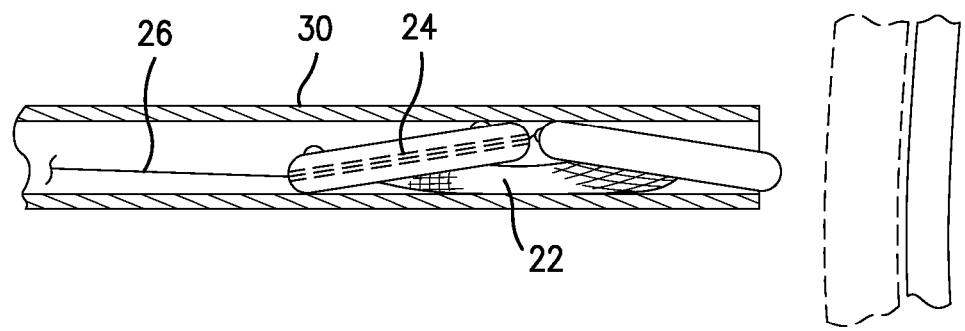
Figure 8:
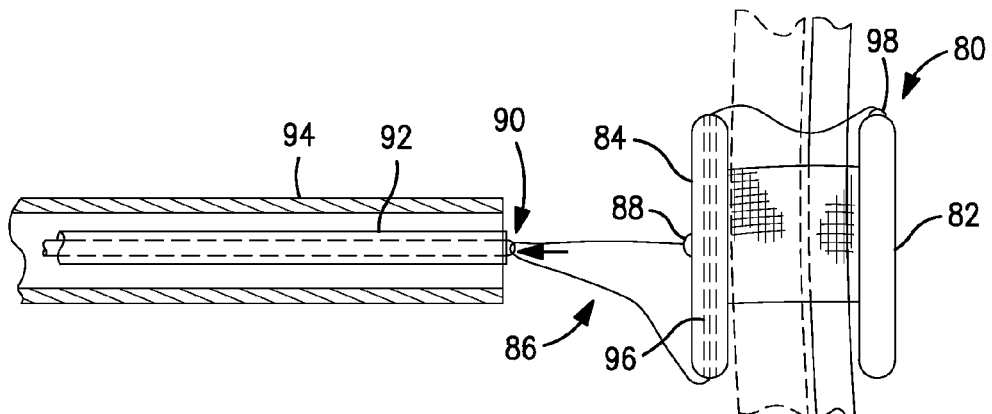
FIGS. 8-11 are partial side and partial cross-sectional views of the removal of a closure device according to a second embodiment of the present invention.
Figure 9:
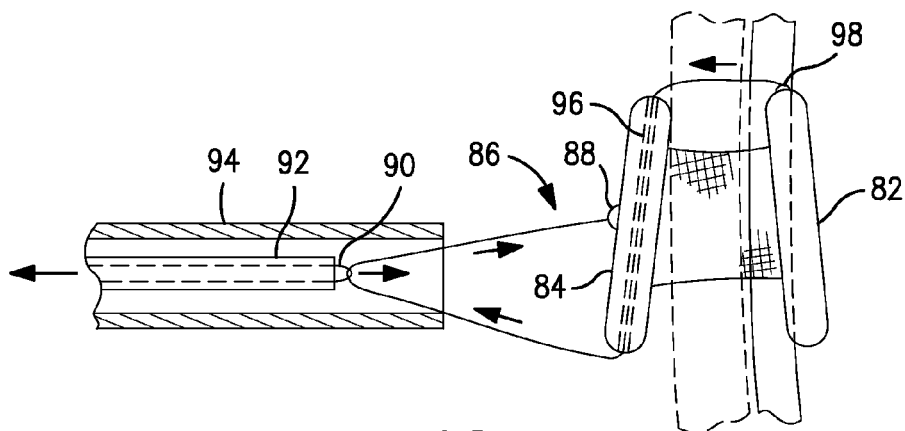
Figure 10:
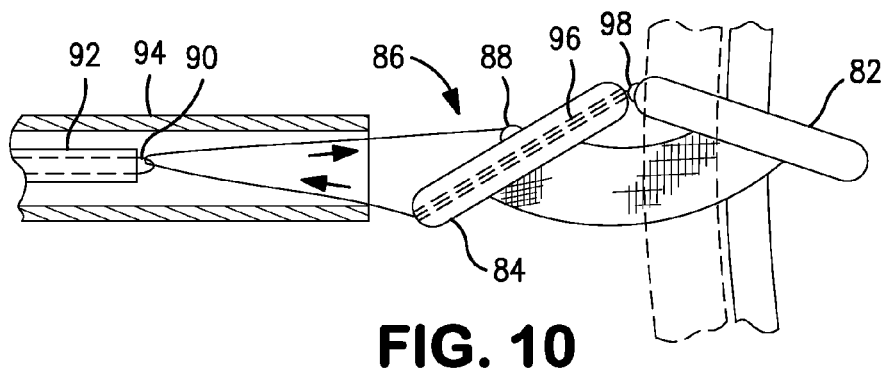
Figure 11:
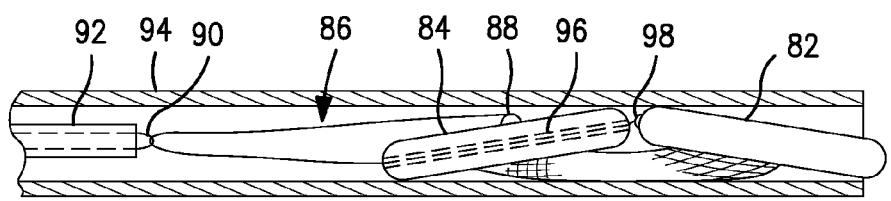

FIGS. 5-7 show how device 10 can be retrieved as described, such as if the practitioner determines that it is not sitting properly. As shown in FIG. 5, delivery sheath 30 is placed up close to anchor 14 while catheter 40 connected to attachment point 16 is pulled. As also shown in FIG. 6, the portion 42 of string 26 connected to attachment point 18 breaks, leaving a loose strand of string. The string also pulls attachment point 20 from anchor 14, but continues to extend through bore 24 of anchor 14 and be rigidly attached to anchor 12. Continued pulling on catheter 40 continues to pull string 26 and causes anchor 12 to rotate as shown to move from a position where it is generally perpendicular to the lengthwise direction of delivery sheath 30 to a sufficient angle where it can be drawn within sheath 30. This pulling action also reduces the length of string between anchors 14 and 12 until they are close to each other or in actual contact. This causes anchor 12 to rotate as shown in a direction opposite to that of anchor 14. Anchor 12 and anchor connector 22 are pulled through the PFO tunnel and back into sheath 30.

In this embodiment, because some of the attachment points have been broken, the device can be retrieved once, but would typically not be redeployed in this form. This embodiment does provide the ability to deliver and retrieve the device using one string and one wire.

FIGS. 8-11 illustrate another embodiment with a device 80 including distal anchor 82 and proximal anchor 84. A string 86 extends from a rigid attachment point 88 on anchor 84 located at about a midpoint along the lengthwise direction of anchor 84, and extends through a loop (or hook) 90 in a delivery catheter 92 within a sheath 94 from this loop, the string extends to an end of anchor 84, through a lengthwise bore 96 and across a PFO tunnel to a rigid attachment point 98 at anchor 82. Loop 90 is movable from a locked position in which the string is held rigidly, to an unlocked position in which the string can move freely. Control for the loop is provided to the operator, e.g., by pulling one end of the loop until the looping wire is fully withdrawn. In this embodiment, with the loop in the locked position, the delivery process is substantially the same as that shown in the embodiment in connection with FIGS. 2-4.

To retrieve device 80, loop 90 is unlocked from its locked delivery position, and delivery catheter 92 is withdrawn. This motion pulls on string 86 and hence anchor 84. Because the distance to attachment point 88 is shorter than the distance to the end of anchor 84, this pulling causes the string lengths to equalize and anchor 84 to rotate. The length of string between anchors 84 and 82 is reduced until anchor 82 rotates in a direction opposite to that of anchor 84 so that the anchors are end to end and can be withdrawn into sheath 94.

This embodiment is useful for recovering the device and can be redelivered. Only one connection to the device is needed.

Figure 12:
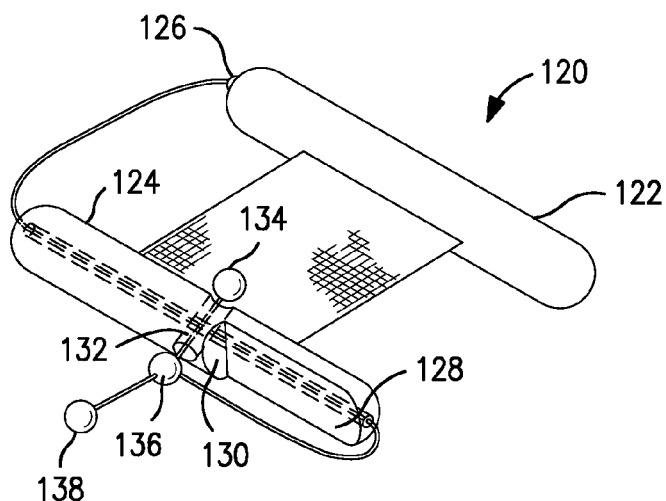
FIG. 12 is a perspective view of a device according to a third embodiment of the present invention.
Figure 13:
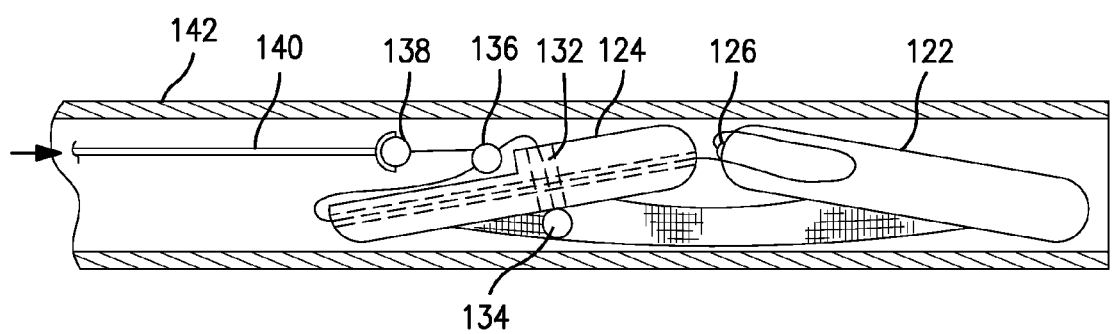
FIGS. 13-17 are partial side and partial cross-sectional views of a device and steps for delivering and removing the device of FIG. 12.
Figure 14:
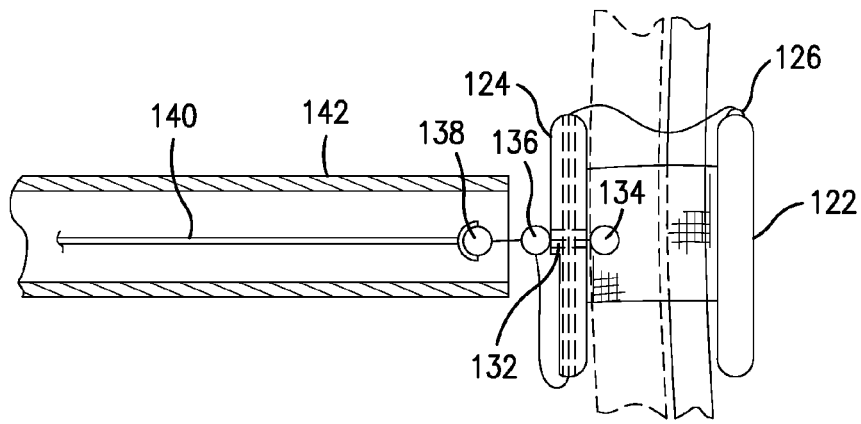

FIGS. 12-17 show yet another embodiment with a device 120. Referring particularly to FIGS. 12 and. 13, distal anchor 122 is similar to that in the prior embodiments and has a rigid attachment point 126 at one end. Proximal anchor 124 for the right atrium is also elongated and generally cylindrical, but it has a cut out to form a flat axial face 128 over a portion of the length at one end, and a flat radial face 130. The cutout provides a smaller profile than without the cutout.

A passage 132 extends along a diameter of anchor 124 with a first ball 134 and a second ball 136 at either end of passage 132 and connected with a string. Ball 136 is slightly larger in diameter than passage 132, but is small enough that ball 134 can be pulled through passage 132 when sufficient force is exerted on it. The ball may deform in the process. An attachment ball 138 is coupled to ball 136 to provide an attachment point for the operator.

These balls can provide distinct functions, such as ball 138 serving as a coupling, and ball 134 serving as a stop. While the contact points and stops are described in this embodiment and in other embodiments as balls and while they are preferably spherical in some embodiments, they can have any shape suitable to form a coupling to a wire in conjunction with a holder that can push or pull them, or a stop, or some other connector. These couplings can be formed differently within one device when there are several couplings; for example, a spherical ball that can be gripped with a grappling hook could be used in one case for a coupling, and a hemispheric piece could be used as a stop.

Figure 15:
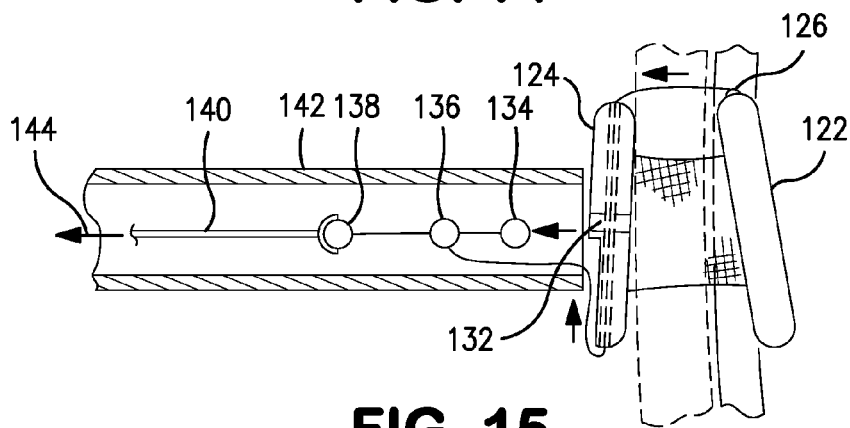
Figure 16:
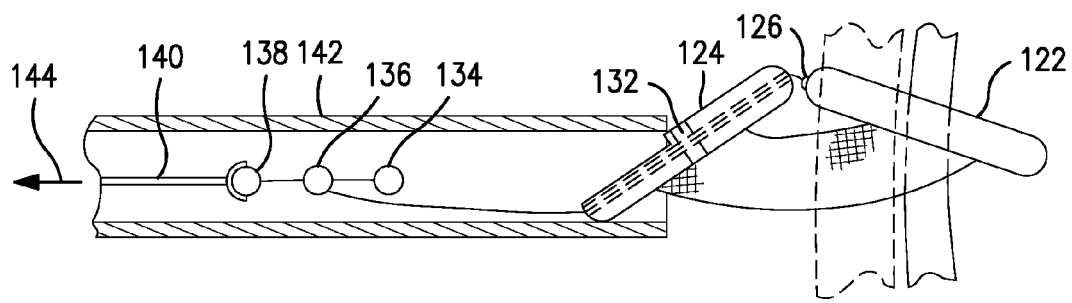
Figure 17:
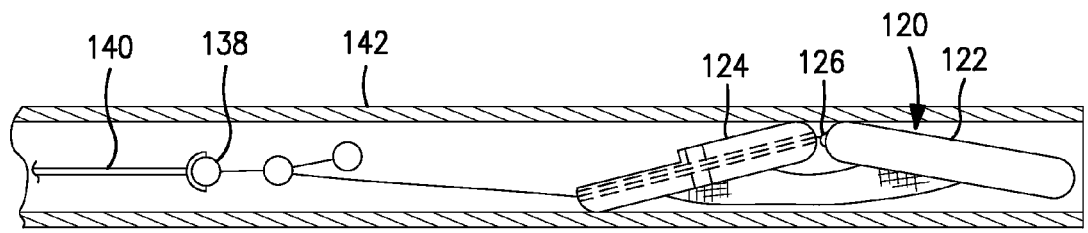

Referring to FIGS. 14-17, the device is shown in a deployed position (FIG. 14) from which it can be retrieved. A wire 140 in a delivery sheath 142 is connected to ball 138 for attachment. As shown in FIG. 15, the pulling force represented by arrow 144 pulls ball 134 through passage 132. After ball 134 is clear of passage 132, sheath 142 is drawn back. Further pulling force causes anchor 124 to rotate and anchor 122 to rotate in a direction opposite to that of anchor 124. As shown in FIG. 17, device 120 can be pulled back fully into sheath 142.

Figure 18:
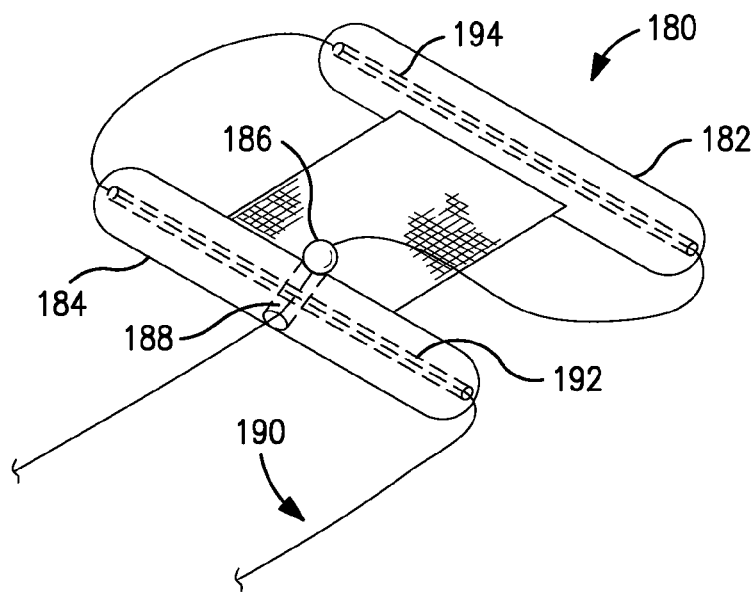
FIG. 18 is a perspective view of a device according to a fourth embodiment of the present invention.

FIG. 18 shows another embodiment of a device 180 with anchors 182 and 184, and with a single ball 186 serving as a connector and a stop on the inner side of a radial passage 188. A string 190 extends to one end of anchor 184, through a lengthwise passage 192, across to anchor 182 (through a PFO tunnel when deployed), through a lengthwise passage 194 in anchor 182, and to a rigid connection with ball 186. Two string ends extend away from the device and are used to control the device, but with ball 186, the string forms an unbroken loop with two ends.

Figure 19:
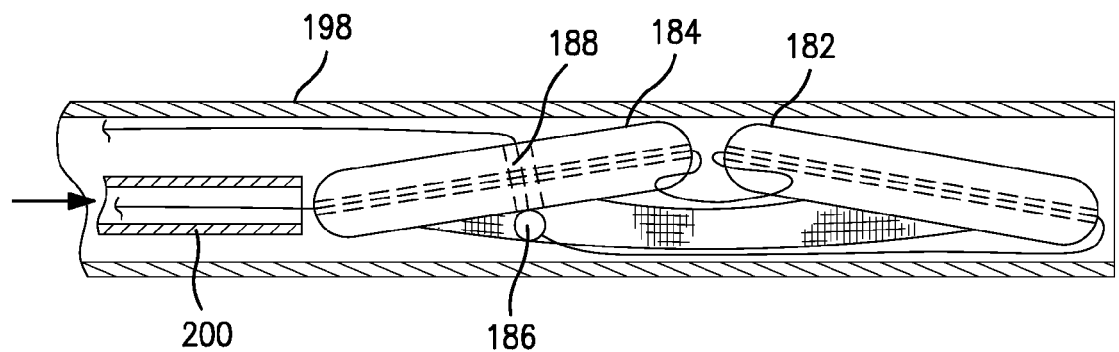
FIGS. 19-22 are partial side and partial cross-sectional views of a device and steps for delivering and recovering the device of FIG. 18.
Figure 20:
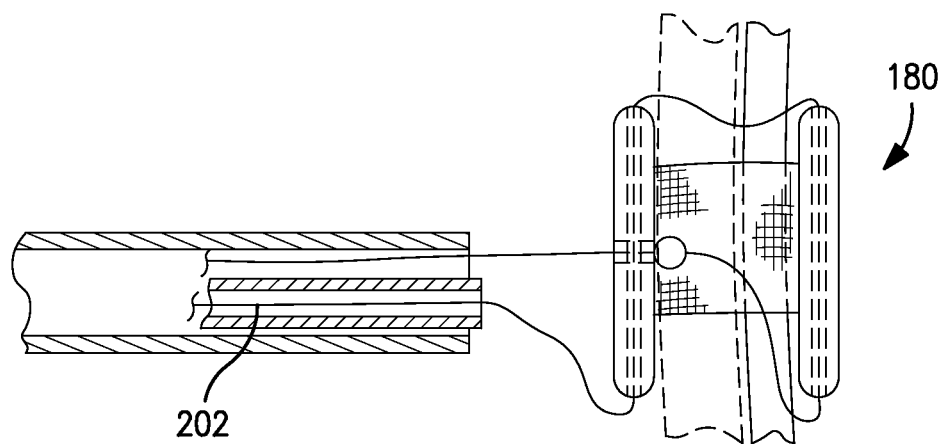

FIG. 19 shows device 180 loaded in a sheath 198 and ready for delivery. A delivery catheter 200 within sheath. 198 provides an inward force to one end of the anchor. The delivery sheath would typically be positioned in the left atrium and retracted to allow anchor 182 to be released within the left atrium. Then, sheath 198 would be withdrawn into the right atrium and further pulled back to release anchor 184 within the right atrium. The resulting deployed device 180 is shown in FIG. 20. After a successful deployment, the strings can be cut.

Figure 21:
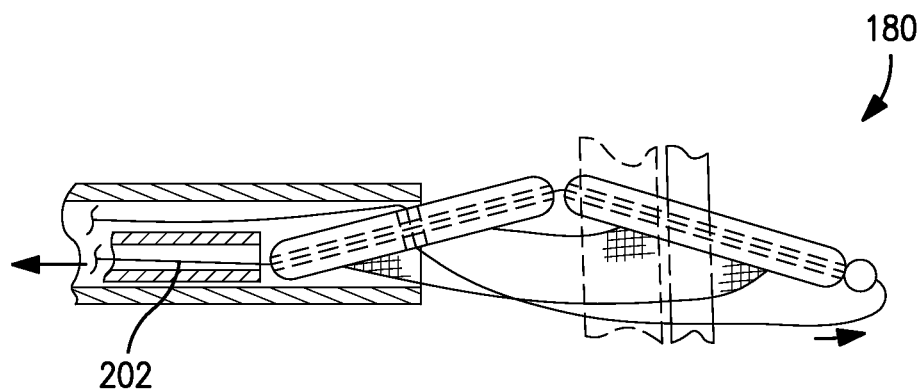
Figure 22:
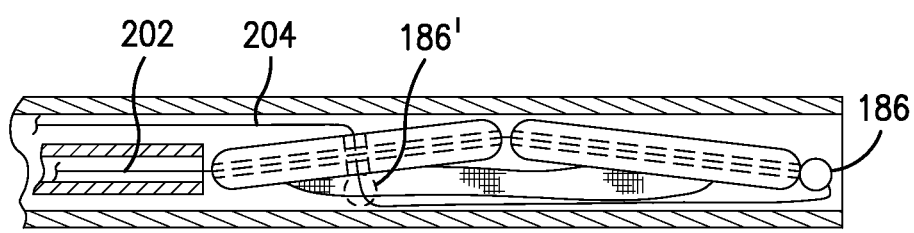

Referring to FIGS. 20-22, to recover device 180, a force is applied to lower end 202 of string 190 in order to rotate anchor 184, causing anchor 182 to rotate in a direction opposite to that of anchor 184 and be returned into sheath 198.

In this embodiment, the device can be redeployed if desired. From FIG. 22, by pulling on upper string 204, ball 186 is moved back against anchor 184 at passage 188 as shown by 186'. At that point. FIG. 22 is substantially similar to FIG. 19, which shows device 180 ready to be deployed.

Figure 23:
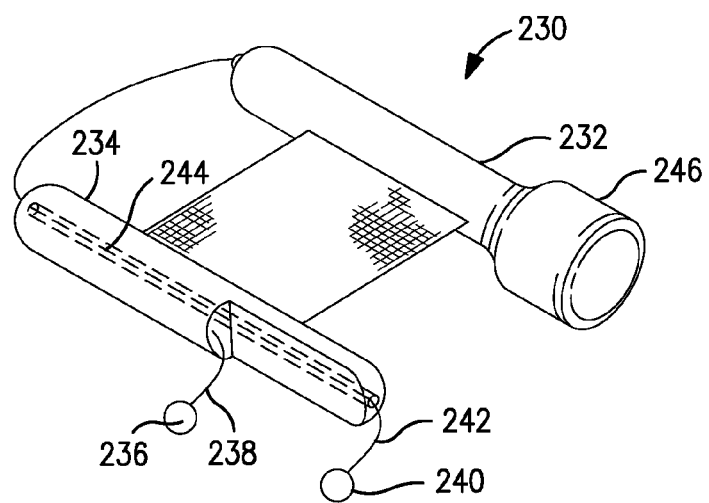
FIG. 23 is a perspective view of a device according to a fifth embodiment of the present invention.

Referring to FIG. 23, a device 230 has a right atrial anchor 234 with a portion cut out of a generally cylindrical side by making a radial cut part way into the anchor and an axial cut along part of the lengthwise direction, with the cuts at right angles to form a cutout section. The resulting faces are similar to those in the device of FIG. 12. In this case, a first ball 236 is connected with a string 238 to the flat axial face that is formed by the radial cut, while a second ball 240 is attached with a string 242 that extends through a lengthwise bore 244 in anchor 234. That string further extends to anchor 232 where there is a rigid attachment at one end. At the other end of left atrial anchor 232 is an enlarged diameter portion 246.

Figure 24:
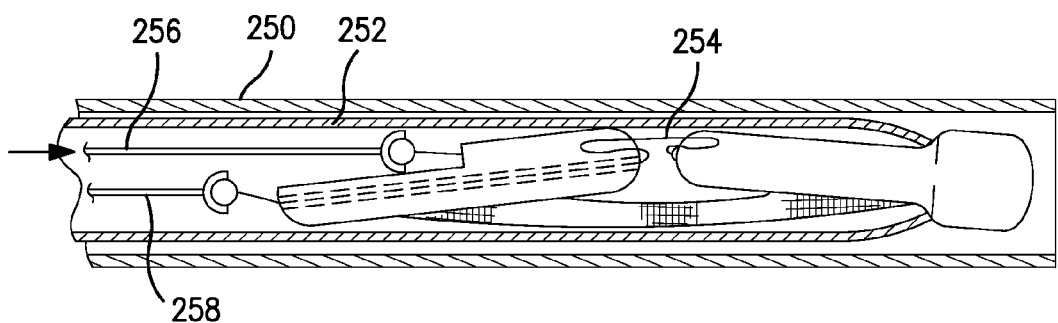
FIGS. 24-28 are partial side and partial cross-sectional views of the device of FIG. 23 and steps for recovering it.

Referring to FIG. 24, when device 230 is loaded in a delivery sheath 250 for delivery, increased diameter portion 246 of anchor 232 is larger than the opening of a delivery catheter 252 and is at the innermost distal end of catheter 252. The string portion 254 between the anchors is shown with some slack, and upper and lower wires 256,258 are connected to respective attachment balls 236,240.

Figure 25:
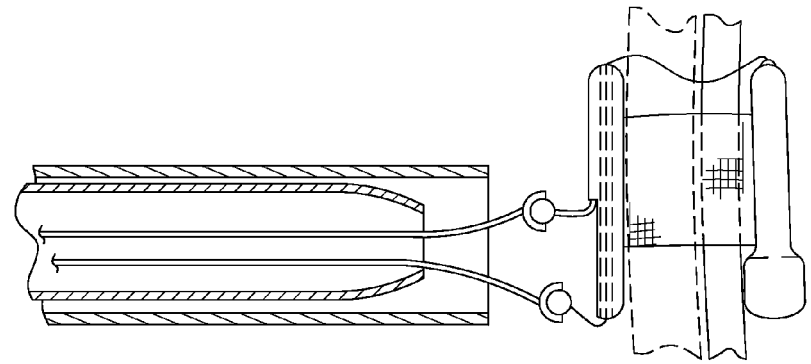

The device is delivered in a similar manner to those described above to a deployed position as shown in FIG. 25. The wires may provide enough stiffness to keep device 230 in place as catheter 252 is removed, or an additional mandrel or catheter (not shown) can be positioned against device 230 to prevent the device from moving toward the proximal end as the sheath is withdrawn toward the proximal end.

Figure 26:
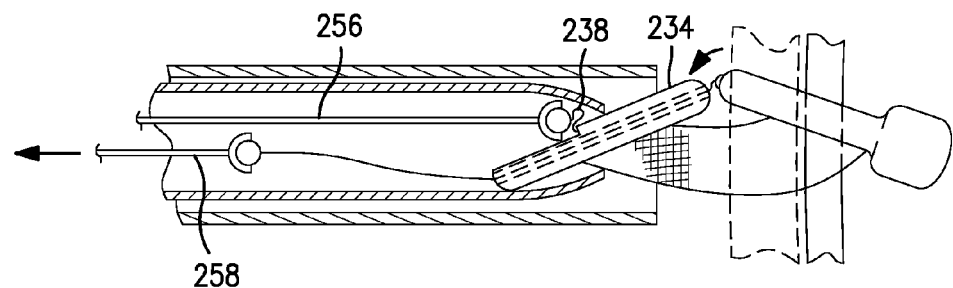
Figure 27:
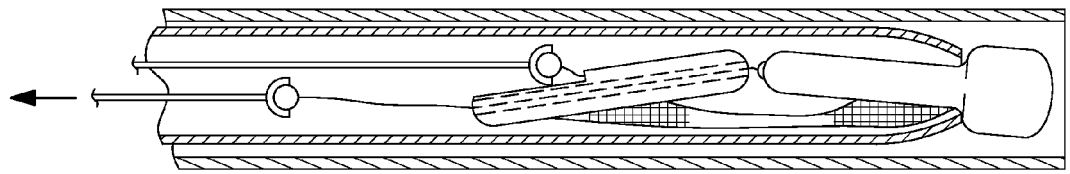
Figure 28:
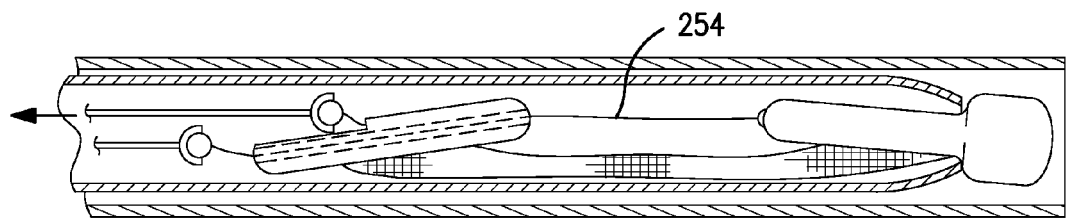

FIGS. 26-28 show the retrieval process for device 230. In this case, lower wire 258 is pulled to cause anchor 234 to rotate. In FIG. 27, the upper wire is pulled to reintroduce slack 254 (FIG. 28). The upper wire is released to allow the device to assume the configuration of FIG. 24. Note that in this position, it can be redeployed into the PFO.

Figure 29:
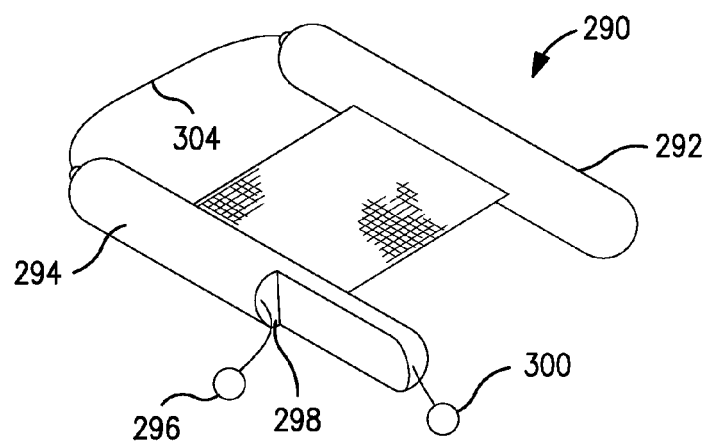
FIGS. 29-34 are a perspective view of a sixth embodiment and partial side and cross-sectional views of the device of FIG. 29 and its delivery and recovery.

FIG. 29 shows another device 290 which has similarities with the embodiment of FIG. 23, with one ball 296 attached to a face 298 formed by the partial radial cut, but with another ball 300 attached to an end of anchor 294. In this embodiment, unlike a number of others, there is no lengthwise bore through either anchor. Anchors 292 and 294 are attached with permanent attachment points with a string 304 at the same end of each anchor, and therefore there is slack that would not be taken up by the operator.

Figure 30:
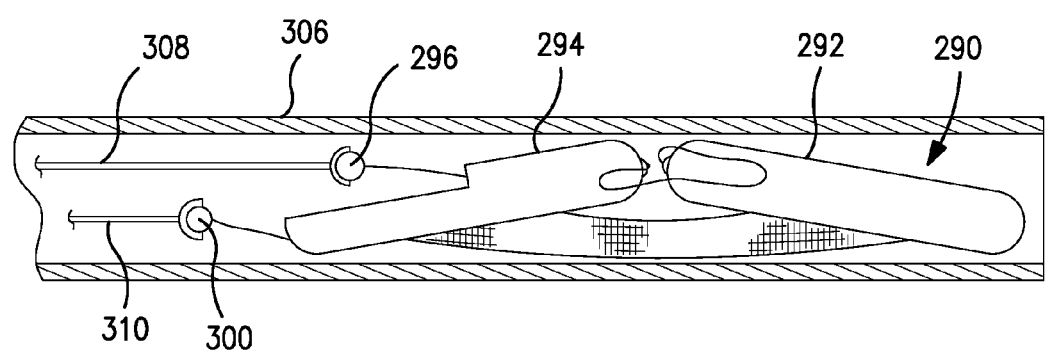
Figure 31:
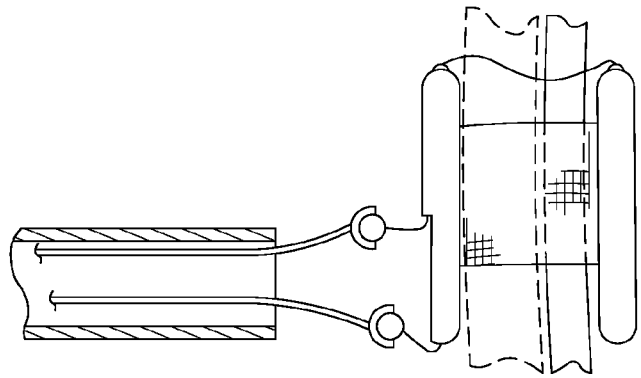
Figure 32:
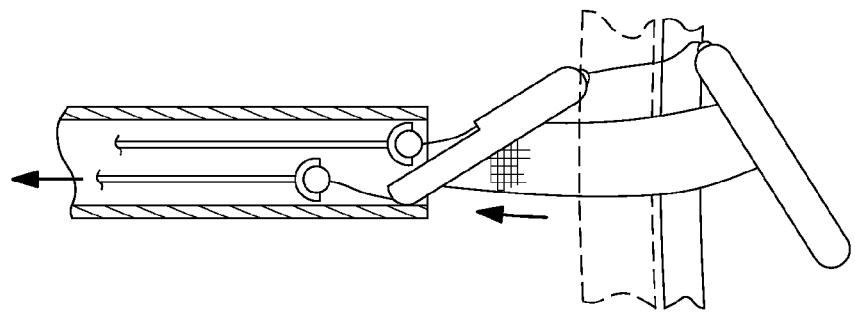
Figure 33:
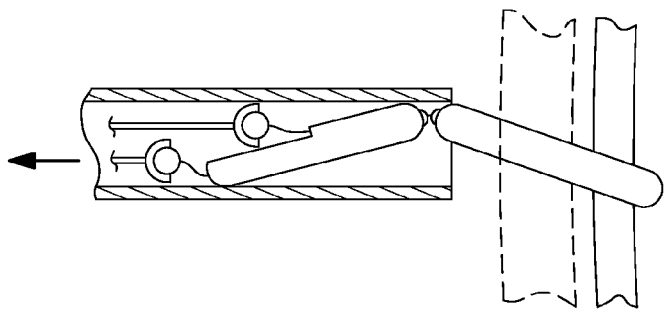
Figure 34:
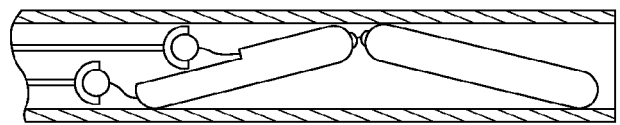

Referring to FIG. 30, device 290 is shown in a sheath 306 and ready for delivery. As indicated above, wires 308 and 310 against respective balls 296 and 300 may be able to provide sufficient resistance to keep the device from being withdrawn as sheath 306 is withdrawn around device 290. If not, an additional device can be inserted to hold device 290 in place as sheath 306 is withdrawn. Device 290 is thus employed in a manner similar to that described above, with the sheath provided in the left atrium, or withdrawn to allow anchor 292 to be positioned, and then further withdrawn into the right atrium to allow anchor 294 to be positioned.

FIGS. 31-34 show the device being retracted into a delivery sheath by pulling on the lowermost wire that is connected to the ball attached at the end of the right atrial anchor. In this embodiment, both anchors rotate in opposite directions until they are end-to-end and drawn into the delivery sheath. From the position in FIG. 34, the device could be redeployed.

Figure 35:
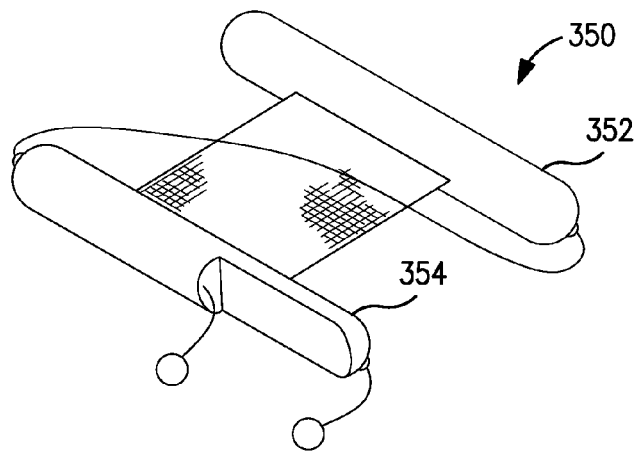
FIGS. 35-37 are perspective views of further embodiments of devices according to the present invention.

FIG. 35 shows another embodiment of a device 350, similar to that shown in FIG. 29, except that the string connecting the anchors extends from one end of one anchor to an opposite end of the other anchor, thereby extending across the anchor connector. This string connection helps to pull anchor 352 so that it rotates in a direct opposite to the rotation of anchor 354.

Figure 36:
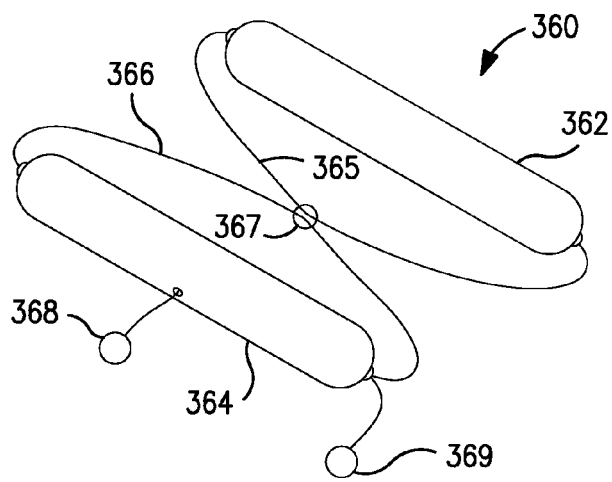

Referring to FIG. 36, in another embodiment, a device 360 has distal anchor 362 and proximal anchor 364 connected together by strings 365 and 366, both of which pass through a loop 367. Anchor 364 also has balls 368 and 369 serving as connection points. In this case, retrieving the device includes providing a connection to ball 369 and pulling to rotate anchor 364, with continued pulling causing rotation of anchor 362. This device would thus be deployed and retrieved in a manner similar to those described above, and could be redeployed multiple times.

Figure 37:
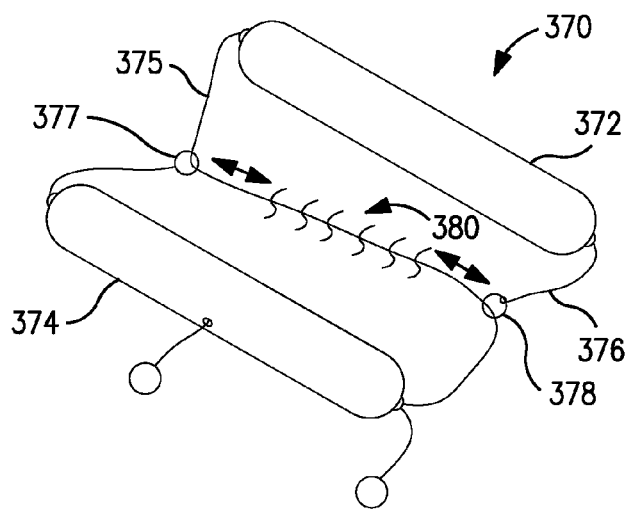

Referring to FIG. 37, a device 370 has a distal anchor 372 and a proximal anchor 374. It also has attachment balls that are similar to those shown in FIG. 36, namely one at one end and one in the middle of the anchor. Distal anchor 372 has strings 375 and 376 extending from each end. String 375 extends from one end of anchor 372, through a loop.

377 that is connected to anchor 374, through a loop 378 connected with a string 376 to another end of anchor 372 and then to the opposite end of anchor 374. String 375 can also have small strings attached to it, referred to here as whiskers 380. These could be provided by being glued to the string, or if the string is in a braided form, the string can be intentionally frayed. The whiskers can help provide some inflammatory effect between tissues, such as between the tissue flaps of a PFO to encourage tissue ingrowth. The device can be delivered and redeployed in a manner similar to that described above.

The closure devices described here can optionally be used along with suturing or stapling techniques deployed from the catheter or sheath.

The devices can use radiopaque fillers or marker bands fabricated from noble metals such as platinum or gold to allow x-ray visualization. These markers can be attached using a variety of common methods, such as adhesive bonding, lamination between two layers of polymer, or vapor deposition where the anchors of the devices can be sewn or stapled to septum primum or secundum for better dislodgment resistance. Also, in some embodiments, an anchor connector can, if desired, be covered with biocompatible glue to adhere to the tissue or can be loaded or coated with drugs or growth factors to promote healing. The glue and also certain drugs can be stored in any cavities in the anchors and released after deployment.

The anchor connector can be mounted to allow the proximal anchor to slide relative to the connector. A biasing spring (not shown), which may be an expandable coil spring, can be formed at an outer end of the central connector to bias the proximal anchor toward the distal anchor when both are.

The various closure devices described herein can include a number of advantageous features. The closure devices preferably have an atraumatic shape to reduce trauma during deployment or removal. In addition, the devices can be self-orienting for ease of deployment. Furthermore, because of the flexible anchor connector, the devices generally conform to the anatomy instead of the anatomy conforming to the devices, which is especially useful in long tunnel defects. The devices also generally have a relatively small profile within the heart after deployment. The flexible anchor connector of the devices can encourage faster tissue ingrowth, and thus faster defect closure. Furthermore, there are generally no exposed thrombogenic components on the left and right atrial sides. The devices can also advantageously include bioresorbable components, which can disappear over time.

Other benefits of the devices can include possible use of a relatively small diameter delivery sheath, use of reduced or no metal mass in the device, ease of manufacturing, cost effectiveness, and overall design simplicity.

Having described embodiments, it should be apparent that modifications can be made without departing from the scope of the invention. For example, while the anchors are shown generally as straight and elongated, they could be curved.

What is claimed is:

1. A septal occluder comprising:
a proximal anchor member for deployment proximate a first side of a septal defect, the proximal anchor having a substantially cylindrical shape, a radial passage extending along a diameter of the proximal anchor, and an axial passage extending along a longitudinal axis of the proximal member;
a distal anchor member for deployment proximate a second side of the septal defect;
a flexible connector connecting the proximal and distal anchor members; and
a removal string for retrieving the device from its intended delivery location, wherein the removal string is connected through the radial passage to a ball stop and connected via the axial passage to the distal member.

2. The occluder of claim 1, wherein the distal anchor member has a substantially cylindrical shape and a longitudinal axis.

3. The occluder of claim 2, wherein a tension applied to the removal string causes the ball stop to pass through the radial passage, thereby permitting the string tension to be transmitted through the axial passage to the distal member, thereby reducing a distance between the proximal and distal anchor members and aligning the longitudinal axes of the proximal and distal anchor members.

4. The occluder of claim 1, wherein a tension applied to the removal string causes the ball stop to pass through the radial passage, thereby causing the occluder to collapse into a form suitable for withdrawal into a delivery sheath.

5. The occluder of claim 1, wherein the distal anchor member has a substantially cylindrical shape and has an axial passage.

6. The occluder of claim 5, wherein each end of the removal string is used for controlling the device.

7. The occluder of claim 5, wherein the removal string is slidingly mounted in the proximal anchor and in the distal anchor.

* * * * *